United States Patent [19]

Leyendecker et al.

[11] Patent Number: 5,063,232

[45] Date of Patent: * Nov. 5, 1991

[54] 2-TERT-BUTYL-4-CHLORO-5-(4-TERT-BUTYLBENZYLTHIO)-3(2H)-PYRIDAZINONE FOR COTROLLING SNAILS AND SLUGS

[75] Inventors: Joachim Leyendecker, Ladenburg; Christoph Kuenast, Otterstadt; Peter Hofmeister, Neustadt, all of Fed. Rep. of Germany

[73] Assignee: BASF Aktiengesellschaft, Ludwigshafen, Fed. Rep. of Germany

[*] Notice: The portion of the term of this patent subsequent to Jan. 1, 2008 has been disclaimed.

[21] Appl. No.: 549,064

[22] Filed: Jul. 6, 1990

Related U.S. Application Data

[62] Division of Ser. No. 377,945, Jul. 11, 1989, Pat. No. 4,981,851.

[30] Foreign Application Priority Data

Jul. 16, 1988 [DE] Fed. Rep. of Germany ....... 3824211

[51] Int. Cl.$^5$ ............................................. A01N 43/58
[52] U.S. Cl. ................................... 514/247; 514/918; 424/84
[58] Field of Search ................. 514/247, 918; 544/241; 424/84

[56] References Cited

U.S. PATENT DOCUMENTS 4,906,627 3/1990 Nakajima et al. .................. 514/247

FOREIGN PATENT DOCUMENTS 0134439 3/1985 European Pat. Off. .
2087723 1/1982 United Kingdom .

OTHER PUBLICATIONS

Chemical Abstracts (106:98153g) 1987.
Chemical Abstracts, Band 93, Nr. 19, 10. Nov. 1980, Seite 192 Spalte 1, Zusammenfassung Nr. 181042d, Columbus, Ohio, U.S.; & JP-A-80 089 205 (Ihara Chemical Industry) 05-07-1980.
Chemical Abstracts, Band 107, Nr. 21, 23. Nov. 1987, Seite 288 Spalte 2, Zusammenfassung Nr. 193071h, Columbus, Ohio, U.S.; & JP-A-62 175 406 (Hokko Chemical Industry) 01-08-1987.

*Primary Examiner*—Frederick E. Waddell
*Assistant Examiner*—Kevin Weddington
*Attorney, Agent, or Firm*—Oblon, Spivak, McClelland, Maier & Neustadt

[57] ABSTRACT

Snails and slugs are controlled by a method in which the plants to be protected from molluscs, or the environment of the said plants, are or is treated with 2-tert-butyl-4-chloro-5-(4-tert-butylbenzylthio)-3 (2H)-pyridazinone I

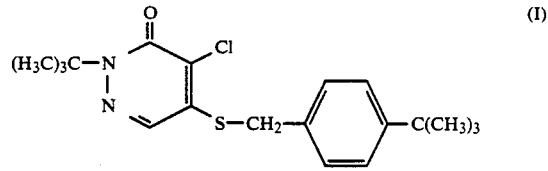

Snail and slug baits or seed dressings contain the active ingredient I.

4 Claims, No Drawings

2-TERT-BUTYL-4-CHLORO-5-(4-TERT-BUTYL-BENZYLTHIO)-3(2H)-PYRIDAZINONE FOR COTROLLING SNAILS AND SLUGS

This is a division of application Ser. No. 07/377,945, filed on July 11, 1989, now U.S. Pat. No. 4,981,851.

The present invention relates to a method for controlling molluscs, in which the plants to be protected from molluscs, or the environment of the said plants, are or is treated with 2-tert-butyl-4-chloro-5-(4-tert-butylbenzylthio)-3(2H)-pyridazinone I

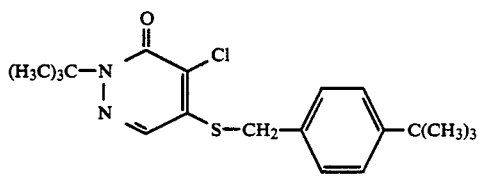

Snails and slugs are major pests in temperate, subtropical and tropical crops. For various reasons, for example because of quarantine regulations (Parella, M. P., Robb, K. and Morishita, P.: Calif. Agriculture 1985, Jan./Feb., 6-8), snail and slug control is becoming increasingly important.

EP-A-134 439 discloses that 2-tert-butyl-4-chloro-5-(4-tert-butylbenzylthio-3(2H)-pyridazinone possesses, inter alia, excellent insecticidal and acaricidal properties. This publication does not indicate any molluscicidal action of this substance.

It is an object of the present invention to provide a novel agent and a method for controlling snails and slugs.

We have found that this object is achieved and that an effective preparation against snails and slugs, for example one which can be formulated as a broadcasting agent, is obtained according to the invention by using the 3(2H)-pyridazinone derivative I defined at the outset.

The 3(2H)-pyridazinone derivative I has excellent molluscicidal properties in the case of both slugs and snails and is very suitable for snail and slug control in agricultural and horticultural crops.

The 3(2H)-pyridazinone derivative I can be prepared as described in EP-A-134 439.

Suitable formulations for molluscicides are described in, for example, GB-A-2 087 723, EP-A-190 595, DE-A-35 03 608, DE-A-37 06 358 and DE-A-35 00 468. They generally contain a carrier, an edible substance or a lure, a binder and the active ingredient and, if required, conventional additives, such as preservatives, colorants, repellents, water, organic solvents, surfactants and the active ingredient.

Examples of suitable (solid) carriers are ground natural minerals, such as kaolins, aluminas, talc, chalk, quartz, attapulgite, montmorillonite or diatomaceous earth, and ground synthetic minerals, such as finely divided silica, alumina and silicates; examples of suitable solid carriers for granules are crushed and fractionated natural minerals, such as calcite, marble, pumice, sepiolite, dolomite, synthetic granules of inorganic and organic meals and granules of organic material, such as sawdust, coconut shells, corn cobs and tobacco stalks.

The edible substances present may be any conventional feed substance which can be used in baits of this type. Ground cereals, for example wheat flour, shredded wheat and shredded barley, as well as coarse soybean flour, bran, rice starch, fish meal, meat meal and molasses, are preferred. It is possible for only one edible substance or a mixture of a plurality of edible substances to be present.

All conventional adhesives which can be used for such purposes may be present as binders. Methylcellulose, sugar, dextrin, starch, alginates, glycols, polyvinylpyrrolidone, ligninsulfonate, gum arabic, polyvinyl alcohol and polyvinyl acetate are preferred. One or more binders may be present.

Examples of preservatives, which may or may not be present, are 2-hydroxybiphenyl, sorbic acid, p-hydroxybenzaldehyde, methyl p-hydroxybenzoate, benzaldehyde, benzoic acid, propyl p-hydroxybenzoate and p-nitrophenol.

Examples of colorants which are suitable additives for repelling birds and mammals are inorganic pigments, such as iron oxide, titanium dioxide and Prussian blue, and organic dyes, such as anthraquinone, azo and metal phthalocyanine dyes.

Substances used for attracting soil pests may be any conventional components suitable for this purpose. Aniseed and aniseed oil are examples.

Repellents used for repelling warm-blooded animals, such as dogs and hedgehogs, may be any conventional components suitable for this purpose. Examples are nonanoic acid vanillylamide.

Suitable organic solvents are all organic solvents which can be conventionally used for the preparation of baits. Low boiling organic solvents, such as methanol, ethanol, butanol and methylene chloride, are preferred.

Suitable surfactants are nonionic substances, such as condensates of polyalkylene oxides and alkylphenols and fatty acid polyoxyalkylene esters, for example octylphenoxypolyoxyethanol, cationic substances, such as quaternary ammonium salts, e.g. cetyltrimethylammonium chloride or cetylpyridinium chloride, and anionic substances, such as the sodium salts of the long-chain alkylsulfates, e.g. sodium laurylsulfate, salts of alkylarylsulfates, the sodium salt of desoxycholic acid, the sodium salt of taurocholic acid and the sodium salt of tauroglycocholic acid.

Another preferred form of application is seed dressing using a formulation usually employed for dressings.

The content of active ingredient in the individual application forms may vary within wide limits, for example from 0.001 to 90, in particular from 0.5 to 50, preferably from 1 to 10, % by weight in the case of granular formulations and from 10 to 90% by weight in the case of seed dressings.

The application rate of active ingredient I is in general about 0.3-30, preferably 1-10, kg/ha.

The molluscicidal action of the novel agents covers terrestrial and amphibious snails and slugs, for example those of the genera Deroceras (Agriolimax), Limax, Helix, Helicogona, Cepaea, Milax, Lymnaea (Galba), Achatina, Theba, Cochlicella, Helicarion and Vaginulus. The snail and slug pests include, for example, the slugs *Arion ater, A. lusitanicus, A. hortensis, Agriolimax reticulatus, Limax flavus, L. maximus, Milax gagates, Mariella dursumierei, Helicarion salius, Vaginula hedleyi* and *Pamarion pupillaris* and the snails *Helix aspersa* spp., *Cepaea nemoralis, Theba pisana, Achatina fulica, A. zanzibarica, Bradybaena* spp., *Cochlodina* spp., *Helicella* spp. and *Euomphalia* spp.

FORMULATION EXAMPLE 1

2 kg of 2-tert-butyl-4-chloro-5-(4-tert-butylbenzylthio)-3(2H)-pyridazinone, 8 kg of calcium stearate, 0.2 kg of sodium benzoate, 20 kg of chalk, 0.5 kg of a blue dye and 63.3 kg of wheat bran were mixed in a mixer. This mixture was then moistened with sufficient water in a kneader and kneaded. The moist mixture was then molded in an extruder to give snail and slug bait granules having a diameter of 3 mm, which were dried at not more than 60° C.

FORMULATION EXAMPLE 2

To prepare a seed dressing,
480 g of 2-tert-butyl-4-chloro-5-(4-tert-butylbenzylthio)-3(2H)-pyridazinone,
20 g of commercial phenolsulfonic acid/urea/formaldehyde condensate,
40 g of ethylene/propylene block copolymer having a molecular weight of 10,000,
2 g of xanthan gum,
0.5 g of Rhodamine FB,
80 g of 1,2-propylene glycol and
5 g of silicone antifoam
were mixed, and the mixture was made up with water to 1 liter.

EXAMPLES OF USE 5 slugs were placed in each Petri dish (diameter 94 mm) and a lettuce leaf ($\simeq 1$ g) which had been dipped in an active ingredient solution of the stated concentration beforehand was added. All experiments were placed in a conditioned chamber at 20° C. and with an L/D (light/darkness) cycle of 18:6 hours. After 4 days, the mortality of the slugs was determined.

The test results are summarized in Tables A and B.

TABLE A

| Compound | Arion hortensis (garden slug) 2–3 cm body length | |
|---|---|---|
| | Concentration % | Number of dead slugs |
| I | 0.1 | 5 |
| | 0.04 | 5 |
| | 0.02 | 5 |
| | 0.01 | 5 |
| Untreated | — | 0 |

TABLE B

| Compound | Deroceras reticulatum (field slug) 2–3 cm body length | |
|---|---|---|
| | Concentration % | Number of dead slugs |
| I | 0.1 | 5 |
| | 0.04 | 5 |
| | 0.02 | 0 |
| | 0.01 | 0 |
| Untreated | — | 0 |

We claim:

1. A snail or slug bait which contains a molluscicidally effective amount of 2-tert-butyl-4-chloro-5-(4-tert-butyl-benzylthio)-3(2H)-pyridazinone and an edible bait capable of attracting molluscs;
  wherein said edible bait is selected from the group consisting of ground cereals, wheat flour, shredded wheat, shredded barley, coarse soybean flour, bran, rice, starch, fish meal, meat meal, and molasses.

2. The snail or slug bait of claim 1, which contains from about 0.0001 to 90% by weight of 2-tert-butyl-4-chloro-5-(4-tert-butylbenzylthio)-3(2H)-pyridazinone.

3. A molluscicidal composition, which comprises a carrier, and edible bait capable of attracting molluscs and a molluscicidally effective amount of 2-tert-butyl-4-chloro-5-(4-tert-butyl-benzylthio)-3(2H)-pyridazinone of the formula I:

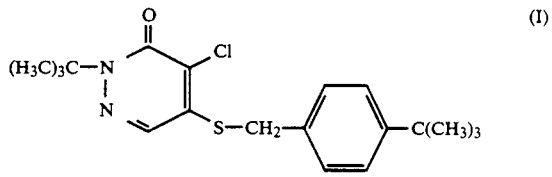

wherein said edible bait is selected from the group consisting of ground cereals, wheat flour, shredded wheat, shredded barley, coarse soybean flour, bran, rice, starch, fish meal, meat meal, and molasses.

4. The molluscicidal composition of claim 3, which contains from about 0.001 to 90% by weight of the compound of formula I.